United States Patent [19]

Jorgensen et al.

[11] Patent Number: 5,107,467

[45] Date of Patent: Apr. 21, 1992

[54] ECHO LOCATION SYSTEM FOR VISION-IMPAIRED PERSONS

[75] Inventors: Adam A. Jorgensen, Oakland Park, Fla.; Otto A. Jorgensen, Old Lyme, Conn.

[73] Assignee: Jorson Enterprises, Inc., Fort Lauderdale, Fla.

[21] Appl. No.: 688,305

[22] Filed: Apr. 22, 1991

Related U.S. Application Data

[63] Continuation-in-part of Ser. No. 508,594, Apr. 13, 1990, abandoned.

[51] Int. Cl.⁵ .............................................. G01S 15/00
[52] U.S. Cl. ...................................... 367/116; 367/99
[58] Field of Search ................................ 367/116, 99

[56] References Cited

U.S. PATENT DOCUMENTS

| | | | |
|---|---|---|---|
| 2,500,638 | 3/1950 | Krauth | 177/352 |
| 2,580,560 | 1/1952 | Larsen | 367/95 |
| 3,366,922 | 1/1968 | Kay | 367/102 |
| 4,292,678 | 9/1981 | Kay | 367/102 |
| 4,712,003 | 12/1987 | Ban et al. | 250/221 |
| 4,761,770 | 8/1988 | Wonky | 367/116 |
| 4,907,136 | 3/1990 | Jorgensen | 367/99 |

*Primary Examiner*—Daniel T. Pihulic
*Attorney, Agent, or Firm*—Oltman & Flynn

[57] ABSTRACT

Echo locating apparatus for a vision-impaired person which includes: a sound emitter for emitting a stream of sound bursts of ultrahigh frequency; at least one receive channel having a microphone for receiving echoes of the sound bursts and generating echo signals; an echo profile detector for generating an echo profile signal of each echo signal; a delay circuit for adding a variable delay to the echo profile signal, wherein the variable delay increases with the distance to the reflecting at a diminishing rate of increase. The sound burst emitter is preferably arranged to emit a beam of sound bursts having a given beam angle that can be pointed in any direction.

19 Claims, 5 Drawing Sheets

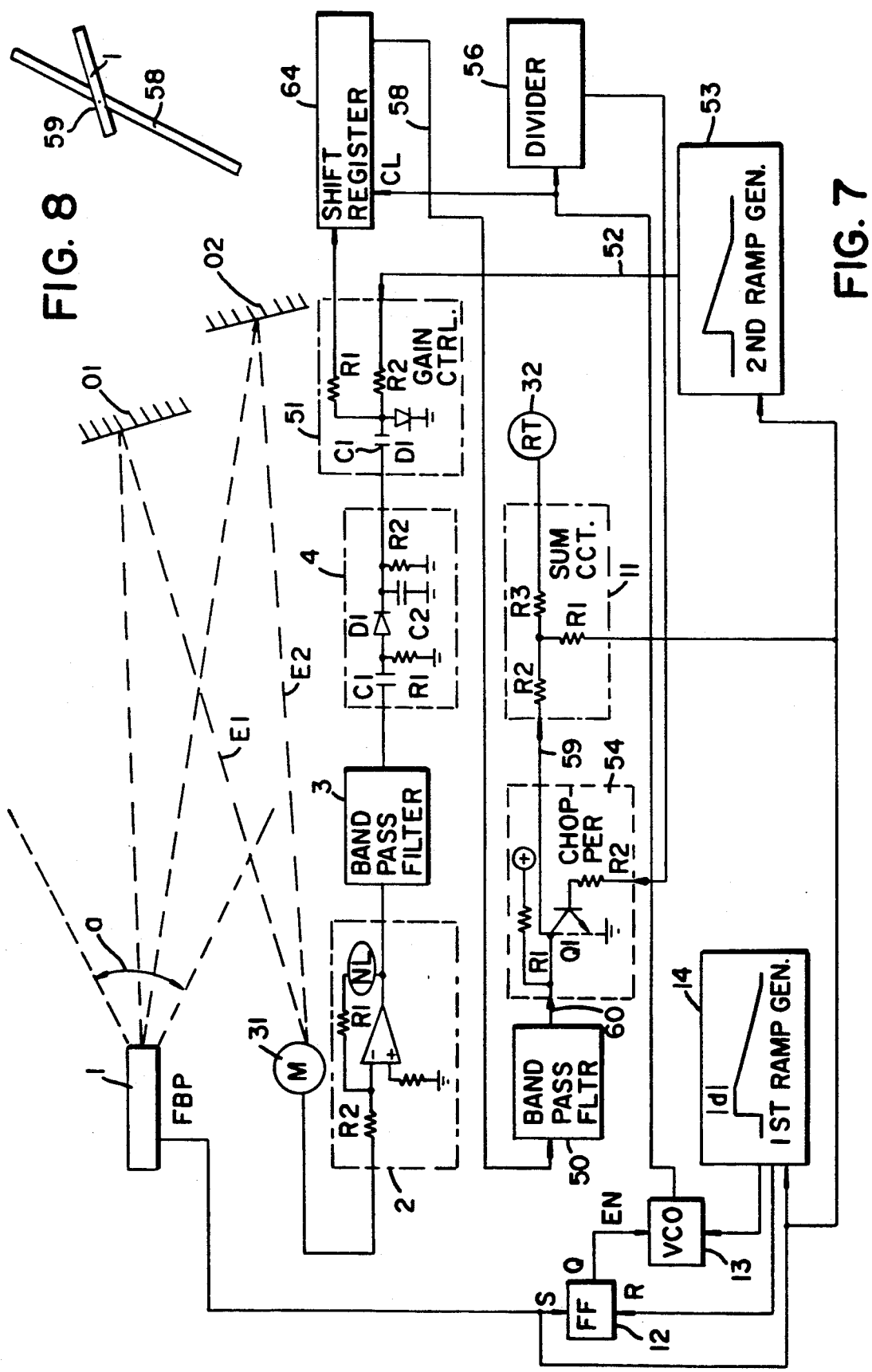

ECHO LOCATION SYSTEM FOR VISION-IMPAIRED PERSONS

This application is a continuation in part of U.S. Pat. No. 508,594 filed Apr. 13, 1990, now abandoned.

BACKGROUND AND PRIOR ART

The invention relates to devices to aid blind or vision-impaired persons to orient themselves in relation to surrounding objects.

The invention is based on the knowledge that most people posses an innate ability to orient themselves in relation to their surroundings by means of their binaural sense of hearing. This sense enables a person to perceive echoes coming in various directions from walls and obstacles. This ability, however, is only marginally useful to people mainly due to two problems, namely that the initial sounds that create the echoes momentarily "numb" the sensitivity of the ear so that the echo which is much more faint is not heard distinctly, and secondly that each echo, when reflected from nearby objects, arrives so short a time after the initial sound that the time difference is imperceptible. Several inventors have disclosed acoustic devices for aiding blind or vision-impaired persons by acoustic means. For example, U.S. Pat. No. 2,500,638 discloses a system of supersonic pulse transmission, wherein the reflected echoes are modulated to a pitch that depends on the distance to reflecting obstacles. U.S. Pat. No. 4,761,770 discloses a supersonic echo locating system wherein reflected pulses are described as being stretched in time by a certain factor, e.g. 32, thereby increasing the delay of received echoes to improve and enhance the perception of the echoes and thereby the distance to reflecting objects. In order to make the stretched echoes better perceptible, they are modulated by a white noise signal. The echo locating systems of the prior art, however suffer from the drawback that simply stretching the time axis for reflected echoes by a given factor does not simultaneously provide good perception of echoes from nearby objects and more distant ones because objects only few feet away must be stretched significantly in order to be perceived as being separate from the originating sound, while echoes from more distant objects become unreasonably stretched and thereby lose the character of an echo. In addition the stretched echoes must be modulated to be audible, which causes a blurring in the perception of overlapping echoes.

U.S. Pat. No. 4,907,136, of which the instant disclosure is a further development, discloses a system based on providing time-stretching means that include the sum of a fixed and a variable delay to the echo signal, wherein separate apparatus is provided for each of these functions. The instant application shows that these functions can be combined into common apparatus and that still better performance can be attained with common apparatus with a reduced investment in components, space and current drain. It is accordingly an object of the instant invention to overcome the drawbacks of the known art and thereby provide an acoustic echo-locating system for vision-impaired persons, which provides simultaneously improved distance perception of nearby as well as more distant objects and at the same time enables a blind person to form in his or her mind a mental "sound image" of the surroundings.

SUMMARY OF THE INVENTION

In accordance with the instant invention there is provided an echo locating system for a blind person, which includes means for emitting sound bursts of a suitable, preferably inaudible ultrasonic frequency toward objects, echo receive means which include at least one receive channel that has a microphone for receiving the echo and generating an echo signal for each sound burst received with a certain actual round trip delay caused by the propagation delay of sound waves in air, and means for adding a further delay as described in more detail below. The echo signal is typically a composite of many echoes reflected from objects located at various distances from the microphone and echoes that have been bounced several times from different objects. The composite echo has an echo profile that is recovered as an echo profile signal by an echo profile detector, which removes the sound burst frequency, and makes the echo signal audible. The echo profile signal is connected to a variable delay circuit for adding the further delay to the echo profile signal. The further delay is a variable increasing delay, which increases according to a certain rule with the distance to the reflecting object(s). A fixed delay may be added which is long enough to give a distinctly perceptible echo from very nearby objects.

In one mode of the invention the variable delay may be increasing at a fixed rate of for example three times the round trip delay. At such a relatively low rate of increase, the echo profile is stretched only by a factor of e.g. three and therefore remains audible and retains its character as an audible echo which does not need to be modulated to remain audible. In this mode the perception of distances is very distinct for objects at both short ranges such as a few feet and remains distinct at ranges up to about 15 to 20 feet, which is somewhat similar to a seeing person's visual distance perception.

In a still better mode of the invention the variable delay is arranged such that it is increasing at a decreasing rate of increase. In this mode still better range perception is attained at both short ranges and ranges beyond the 15 to 20 feet range.

The echo profile signal received and heard by the blind person accordingly in heard with a total delay consisting of the actual round trip delay, the fixed delay and the variable delay. The fixed delay is selected such that the blind person hears echoes from nearby objects as distinct echoes, and the additional variable delay is selected such that the echoes from more distant objects are heard with a delay increasing with the distance.

In the instant invention it is not necessary nor desirable to add modulation to the echo profile signal since the echo signal is stretched only to a relatively small degree, compared to the stretching required with the prior art. Moudulation as shown and required in the prior art only causes a blurring of the individual components of overlapping echo signals and prevents the person from perceiving the individual echoes and their conponents as range information, and thereby prevents the blind person from forming a mental sound image of the surroundings.

As a further feature, the invention is arranged as a two-channel system with a receive channel for each ear of the user. In this case the user will enjoy the benefit of binaural hearing which further aids in enhancing the distance perception and forming a mental sound image.

As a still further feature, means are provided for feeding back an audible feedback pulse that is synchronous with each emitted sound burst, which enables the blind person to hear the initial sound burst, suitably attenuated, followed by the delayed echoes to further enhance the perception of the received echoes as distance information.

In accordance with still another feature of the invention, the sound emitter is a hand-held device which projects a beam of sound bursts, wherein the beam angle may be adjustable by the user.

These and other features of the invention are described in the following specification when taken together with the figures of the drawing. It is to be understood, however that the invention is not limited to the features described since the invention is capable of further features that will be obvious to a person skilled in the art to which it pertains and are within the scope of equivalencies of the claims.

BRIEF DESCRIPTION OF THE DRAWING

FIG. 7 shows a block diagram similar to FIG. 3 further including a gain control circuit.

DETAILED DESCRIPTION OF THE PREFERRED EMBODIMENTS

Figure 1A:
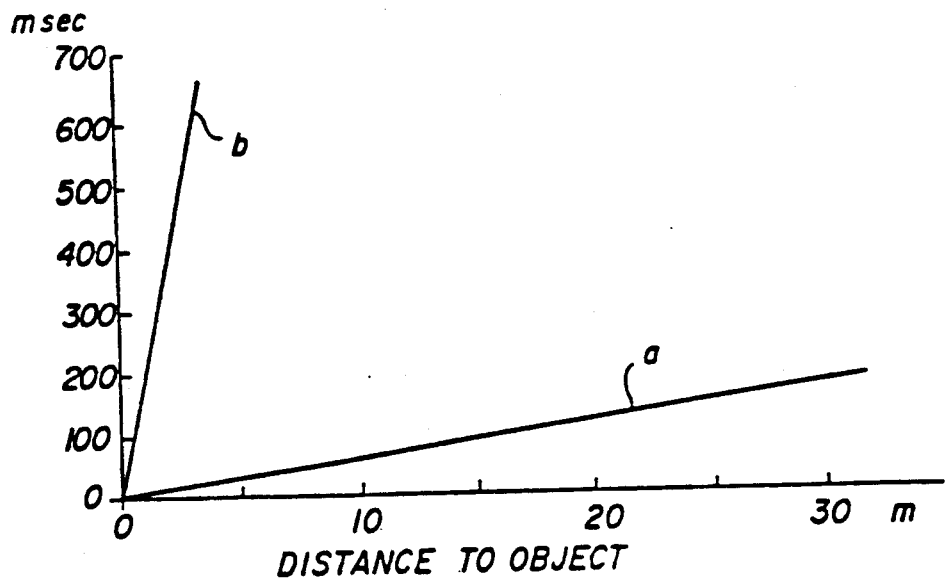
FIG. 1a shows graphs of the round trip delay of a sound burst and of the delay added according to the known art.

FIG. 1a shows in curve "a" the actual round trip delay of an echo in milliseconds, as a function of the distance in meters, to a reflection object. The velocity of sound in air is close to 340 meters/second. Curve "a" accordingly shows the round trip delay to an object 30 meters away as being approximately 176 msec, and the delay to an object 3 meters away as being 17.6 msec. Tests have shown that a delay of approximately 50 msec is required to perceive an echo as being distinct from the originating sound burst creating it. Using a constant factor for the delay increase has the drawback that in order to perceive echoes from objects as close as for example 0.5 meter a large factor of 32 times is required. This large increase in the delay causes objects being only as far away as 5 meters to be as large as 928 msec. An echo of this magnitude loses its character of being an echo, especially when it is received in a mixture of ambient room noises, and as a result the blind person loses the mental perception of distances to objects even as close as 5 meters, due to the delay having a constant rate of increase such as 32 times, in other words having a fixed rate of delay without the additional fixed delay.

Another drawback to the use of only a fixed and therefore a large rate of delay is that the echo profile also becomes extended, i.e. "smeared", and therefore becomes virtually inaudible so that it must be modulated by some sound or noise in order to become audible. Modulation changes the audible perception of the echo and as a result the innate ability to form a "sound picture" is lost.

Figure 1B:
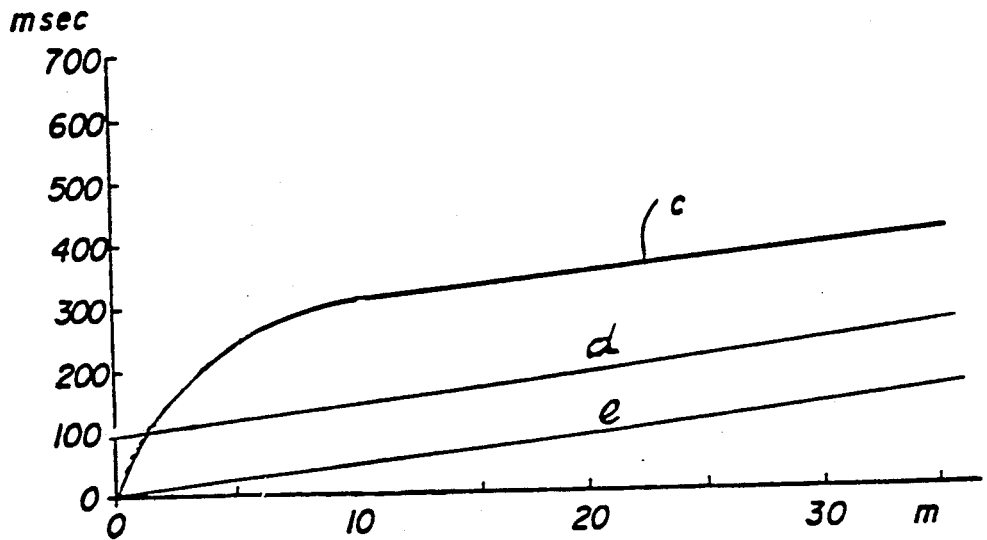
FIG. 1b shows a graph of the added delay according to the instant invention.

FIG. 1b, curve c shows a variable rate delay. The variable delay has a rate of delay increase, which naturally is equal to the slope of the curve c. The curve c has at shorter ranges a greater initial slope as indicated for short ranges where the slope is steep, and the slope, i.e. the rate of increase, decreases as the distance increases, until it becomes virtually linear at greater distances. In this way the profile of the received and artificially delayed echo signal is not significantly extended, i.e. "smeared", and therefore remains audible just like a natural echo and no modulation of the echo signal is required and as a result the received echoes infer to the receiving person a more realistic sense of range, especially with binaural reception.

Figure 2:
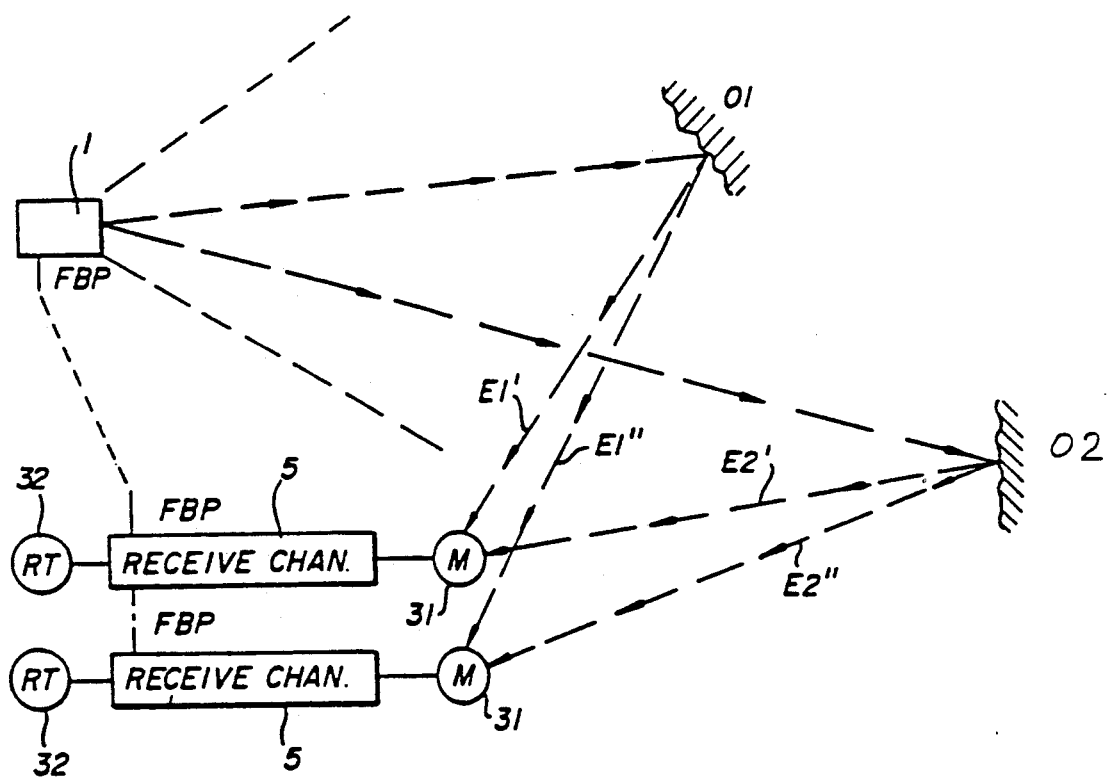
FIG. 2 is an overall block diagram of the instant invention, showing echoes reflected from objects at different distances and directions.

In FIG. 2 a sound emitter 1 radiates sound bursts as indicated by dashed lines into a certain field "of view", which may be a wide angle or narrow angle field of view. Two objects O1 and O2 at different ranges and angles from the sound emitter return respective echoes E1 and E2 to one or two receive channels 5, each having a microphone 31 and a receive transducer 32. The microphones 31 are spaced apart a certain distance and therefore receive echoes E1', E1'', E2', and E2'' from the two objects which are slightly different mainly due to phase differences and therefore labeled with different suffixes and primes. The differences in the echoes enable a person with binaural hearing to subliminally sense distances and directions to reflecting objects, when the echoes have been delayed in accordance with the instant invention.

For each sound burst emitted by the sound emitter 1, a feedback pulse FBP is returned from the sound emitter to each receive channel 5. The feedback may be electrical or may be simply acoustically transmitted to each channel.

Alternatively the feedback pulse can originate from the receive apparatus 5 and be used to trigger the sound bursts from the sound emitter 1.

Figure 3:
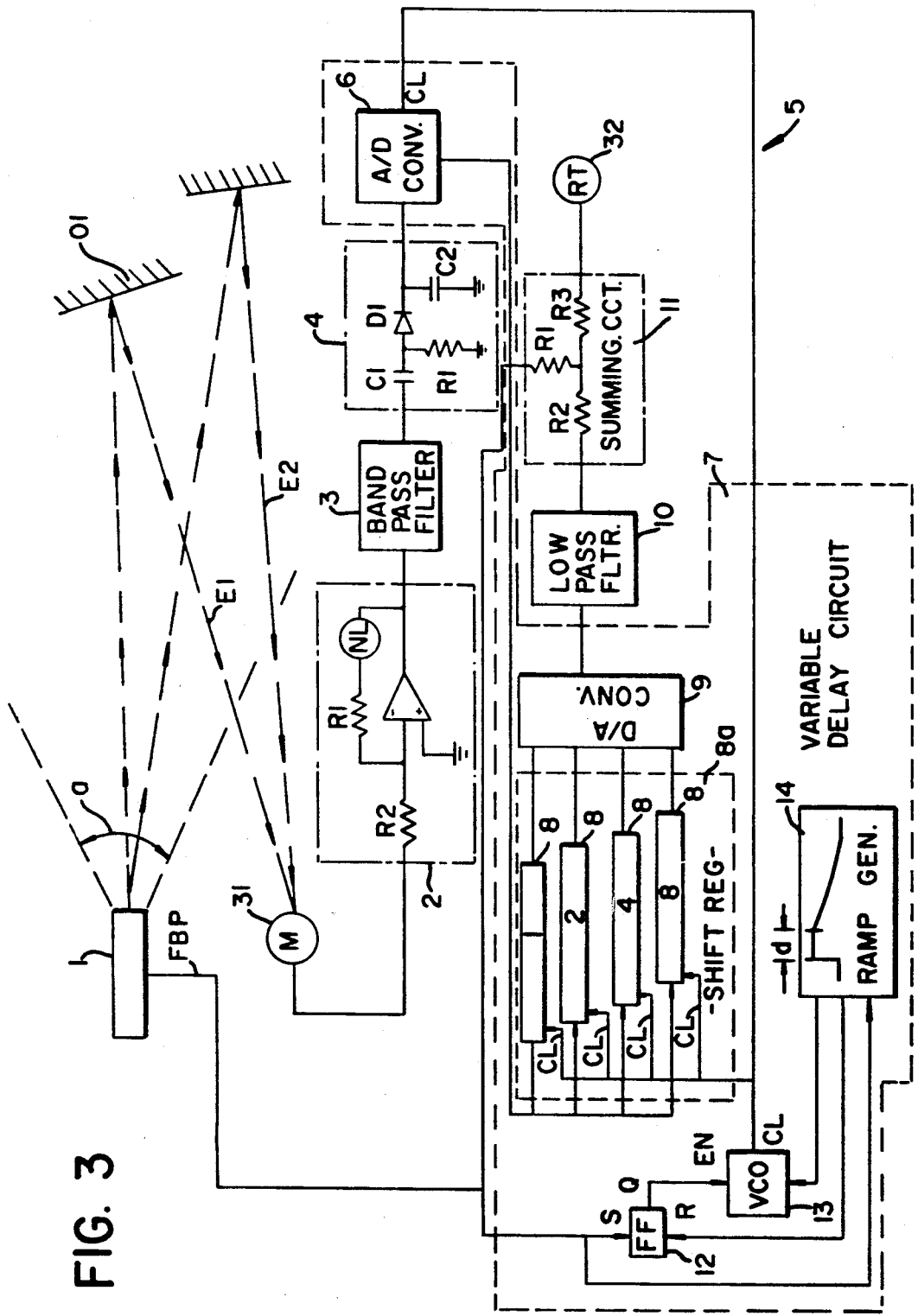
FIG. 3 is a circuit diagram of the delay circuit clocked with a frequency-modulated clock signal, based on the use of digital binary weighted shift registers.

FIG. 3 shows details of one receive channel 5. The microphone 31 receives the echoes E1, E2 and generates an echo signal for each sound burst, connected to the input of an amplifier stage 2, having feedback resistors R1, R2 for gain stability.

The sound emitter emits sound bursts that are advantageously in the ultrasound range beyond the audible range. The received echoes are therefore also inaudible. The feedback network R1, R2 may advantageously also include nonlinear components NL, e.g. diodes so that a logarithmic gain response is attained, which will tend to give lower gain stronger echoes from nearby objects and conversely greater gain for more distant objects. The output of the amplifier stage 2 is connected to a bandpass filter 3, having a passband narrow enough around the selected burst frequency to reject unwanted ambient noise. The output of the bandpass filter 3 is connected to an echo profile detector 4 which restores the echo to an audible signal. The profile detector has a rectifier diode D1 connected to an input network having a capacitor C1 and a resisitor R1 joined to the anode of diode D1 and respectively connected to the output of bandpass filter 2 and ground. A filter capacitor C2 is connected between the cathode of diode D1 and ground. The diode cathode generates the echo profile signal which is in the audible frequency range. The echo profile signal is connected to a variable delay circuit 7, shown in a dashed line box. The first stage of the variable delay circuit 7 is an analog/digital converter 6, which converts the analog echo signal profile into a sampled digital signal consisting of repetitive digital samples consisting of for example four bits each. The sampling frequency CL is of hte Nyquist rate, in other words of a frequency at least twice the highest frequency component of the echo profile signal. The bits of the digital samples are each connected to a respective shift register 8. The shift registers 8 are parallel connected and have binary weightings 1,2,4, and 8. The shift registers have outputs connected to respective inputs of a digital/analog converter 9, which is followed by a lowpass filter 10. The lowpass filter produces a delayed analog output representing the original echo profile delayed a delay time VD, equal to the travel time through the shift registers 8, plus a fixed delay d. The travel time thruogh the shift registers 8 is controlled by a variable shift clock CL, generated by a voltage-controlled oscillator VCO, having a frequency control imput FC, connected to a ramp generator 14, which generates a ramp of a negative slope, shown in FIG. 5, line f. The feedback pulse FBP from the sound vurst emitter 1, which signals the emission of a sound burst, is connected to a set input S of a flip-flop 12, having an output Q, connected to an enable input EN of the VCO 13. When input EN goes active, the VCO starts oscillating at its base frequency, which appears at the clock output CL. The feedback pulse FBP starts the ramp of the ramp generator 14, which in turn generates a ramp signal of a voltage at the frequency control input FC of the VCO 13 which causes an output CL from the VCO of decreasing frequency, or a similar circuit. At the start of the ramp voltage the shift clock CL from the VCO starts to decrease in frequency, which in turn starts an increase in travel time through the shift registers 8. At the end of the ramp signal the ramp generator generates a reset pulse on pin R of the flip-flop 12, causing the VCO to stop oscillating as the enable signal EN goes back to zero. At that time the delay circuit 7 is ready to receive the next echo.

It follows that the delay of the echo signal depending upon the form of the ramp signal will follow a function as shown in curve e in FIG. 1b, if a straight line ramp is provided or curve d if an initial fixed delay of 100 msec is provided, or better still as curve c if a suitably curved ramp is used. It follows that the ramp need not have only negative slope as shown but can have other shapes, e.g. a logarithmic or exponential shape or a composite shape of several types of curves in order to generate delay curves as may be most suitable. If the initial part of the ramp is horizontal, that part becomes a fixed delay.

A summing circuit 11 which is part of the receiving circuit 5 receives the feedback pulse FBP and merges it with the delayed echo profile signal. The output of the summing circuit 11 is connected to a receive transducer 32 which is coupled acoustically to an ear of the blind person. In operation the user hears first the feedback pulse followed by the delayed echo(es). The feedback pulse gives a reference for evaluating the distance to reflecting objects. Other forms of delay circuits may be used. For example a charge-coupled device (CCD) may be used as an analog shift register, combined with a VCO and a ramp generator as described above.

Instead of a shift register it is also possible to use a fixed random access memory in which the samples from the echo signal are written in successively by a time-varying clock and read out again by the same clock.

In operation the user hears first the feedback pulse followed by the delayed echo(es). The feedback pulse gives a reference for evaluating the distance to reflecting objects.

In a binaural arrangement having two delay circuits, it follows that the VCO and the ramp generator can be common to the two delay circuits. Such an arrangement in fact provides a better operation, in that the two echoes E1 and E2 are treated identically so that the minute differences in the two echoes E1 and E2 can be better discerned by the user.

Figure 4:
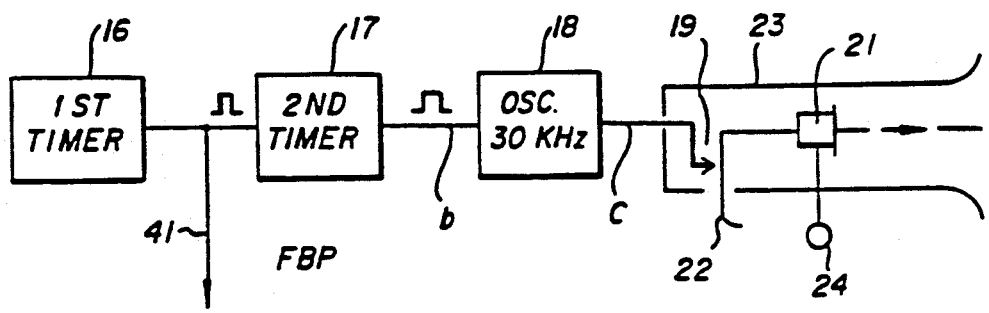
FIG. 4, is a block diagram of a sound burst emitter according to the instant invention.

FIG. 4 is a block diagram of the sound emitter 1. A first timer 16 generates a start pulse for each sound burst. The start pulse may be equivalent to the feedback pulse FBP. It also starts a second timer 17 which controls the duration of each sound burst by means of an enabling signal b connected to an oscillator 18, which in turn generates a signal of e.g. 30 kHz, which is connected to a transmit transducer 21 coupled to the air, thereby generating the sound bursts. The transmit transducer 21 is advantageously housed in a horn 23 which forms the sound bursts into a directed beam. The beam angle can be controlled by sliding the transit transducer 21 axially in the horn 23 by means of a knob 24. A trigger 22 connected to a make contact 19 serves to manually control the emission of the sound bursts.

Figure 5:
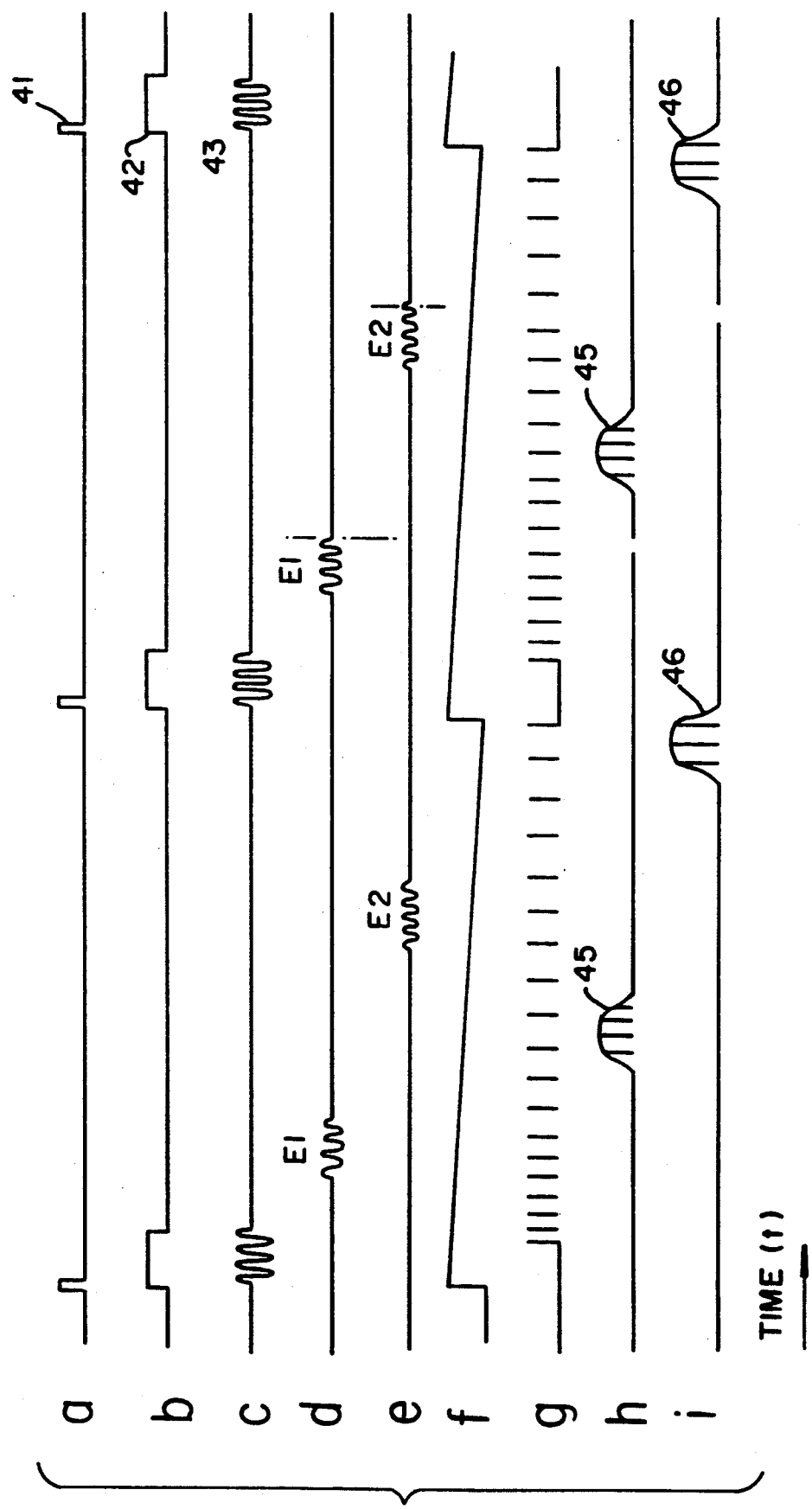
FIG. 5 shows a series of graphs of sound bursts, their echoes and their delayed echo signals as described in the following detailed description of the invention.

In FIG. 5 line "a" pulses 41 are start pulses for the sound bursts which are similar in timing to the feedback pulses FBP. Line "b" shows the enable pulses 42 for the frequency oscillator 18. Line "c" shows the sound bursts as short trains of supersonic sound waves. Lines "d" and "e" show echoes respectively from a nearby and a more distant object. Line "f" shows the ramp pulses with a linear positive slope, starting with a delay "d" from the start pulses 41. Line "g" shows trains of shift pulses 44 with decreasing clock frequency clock frequency from the beginning to the end of the train. Line "h" shows delayed echo signals 45 from the nearby object 01 delayed by the fixed delay d, and line shows delayed echo signals from the more distant object 02.

Figure 6:
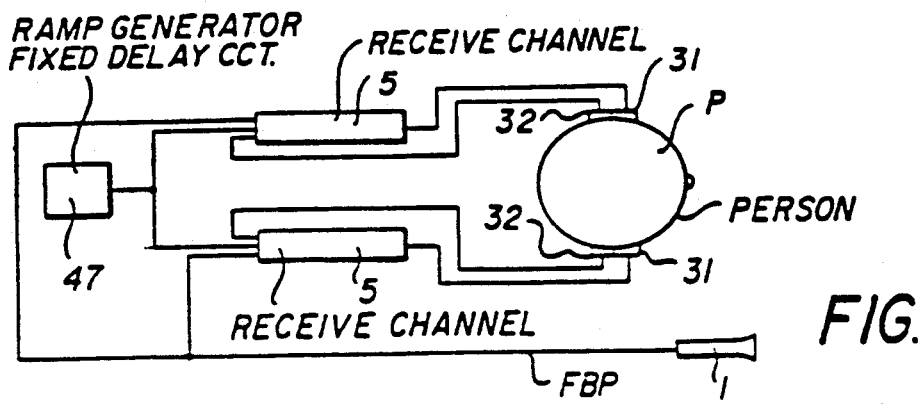
FIG. 6 shows a person provided with apparatus according to the invention. p

FIG. 6 shows a user P provided with a microphone 31 close to each ear and a receive transducer 32 also close to each ear, and a receive channel 5 for each ear, in a binaural arrangement. The voltage controlled oscillator, the ramp generator and the fixed delay circuit are combined in a unit 47 commonly connected to the two receive channels 5. A handheld sound emitter 1 has a feedback pulse lead FBP connected to the two receive channels 5. It is contemplated that all circuitry be realized as micro circuit components so that all circuitry can be fitted into a single pocket or carried on a belt.

A further improvement of the invention is shown in the block diagram of FIG. 7, which is similar to FIG. 3, with the following changes:

A gain control circuit 51 has been added behind the echo profile detector 4, which operates to increase the received level of the echo signal with increasing distance to the reflecting objects in order to overcome the attenuation of the echo profile signal caused by loss in the air at increasing travel distance. The gain control 51 utilizes the variable dynamic impedance of a diode D1, which is controlled by a decreasing output 52 of a second ramp generator 53 operating synchronously with the first ramp generator 14, also controlled by the feedback pulse FBP. With decreasing current through the diode D1, its dynamic impedance increases and the attenuation of the echo signal from the profile detector 4, caused by the shunting effect of the diode D1 decreases in well-known manner, thereby partially overcoming the decrease in signal strength with increasing distance to reflecting objects.

A signal chopper 54 is added behind the shift register 64, which operates to chop the delayed echo profile signal with an audible variable frequency that varies with the distance to the reflecting object, so that echoes coming from nearby objects are heard chopped, i.e. modulated, with e.g. a high frequency pitch, while more distant objects are chopped with a lower frequency pitch. Accordingly, when two reflecting objects that are positioned at different distances such as objects 01 and 02 (FIG. 2), the nearer object 01 is heard first, with a shorter delay and a higher pitch, while the more distant object 02, is heard later with a lower pitch. The separation in both time and pitch contributes to a more distinct perception of different distances than by time separation only. The chopping frequency is advantageously obtained from the variable frequency output of the VCO 13, described above, by suitable frequency division in a frequency divider circuit 56, which is advantageously a conventional binary recirculating counter, set to divide, for example by eight. In a typical system the frequency from the VCO 13 starts at 60 kHz, decreasing to 20 kHz during a complete echo cycle. After being divided by eight the divider 56 generates chopping frequencies from 7500 Hz decreasing to 2500 Hz, which are well within the audible range. The chopper includes an NPN transistor Q1 being driven at its base by the divider 56 so that the signal from the gain control 15 is chopped, i.e. periodically shunted to ground by the transistor's collector-emitter path at the chopping frequency.

The chopped output 59 from the chopper 54 is connected to the summing circuit 11 as described above under FIG. 3. The analog shift register 8a of FIG. 3 is shown in FIG. 7 as a single block 64, that may be realized as a digital binary encoded shift register as shown in FIG. 3, or in other forms. In one suitable form the analog shift register may be a so-called charge-coupled shift register, in which an input signal is shifted via a string of e.g. 2000 stages by means of the variable clock CL, which drives the input signal at a descending speed through the shift register 64 in order to increase the delay through the shift register as described above.

A band pass filter 50 shown in FIG. 3 as a low pass filter 10, set typically to a high cut-off frequency of 9 kHz and a low cut-off frequency of 1000 Hz, restores the output of the analog shift register 64 approximately to its original input profile, and has its output 58 connected to the chopper 54 which has its output 59 connected to the summing circuit 11, which sums the delay echo profile with the feedback pulse FBP as described above under FIG. 3.

It should be noted that the various circuits shown in FIG. 7 need not be arranged in the sequence shown. The chopper 54 can, for example, be located before the analog shift register 64. The gain control 51 may be located before or after the analog shift register, and still other arrangements may be used.

In FIG. 5, lines h and i, the echo profile signals 45 and 46 are shown chopped by means of vertical lines drawn through the signal. As shown, the chopping frequency decreases with increasing distance, as described above, i.e. echo profiles 45 are shown with a higher chopping frequency than profiles 46. It follows that the chopping frequency could alternatively be generated by a separate second VCO instead of being divided from the clock frequency. Also, the chopping frequency may alternatively be arranged to be low for nearby objects going to a high pitch for more distant objects, instead of going from high to low as described above.

In the physical arrangement of the invention, it is advantageously provided that the sound emitter 1 is coupled to a cane 58 as shown in FIG. 8. The sound emitter 1 may be coupled to the cane 58 at a pivot point 59 so that the user may grasp the sound emitter 1 with one hand, and the cane 58 with the other hand for added comfort and security.

We claim:

1. Echo locating apparatus for a vision-impaired person for sensing distances and directions to reflecting objects, comprising: means for emitting sound bursts of a given frequency; echo receive means including at least one receive channel, having a microphone for generating an echo signal for each sound burst received; an echo profile detector for generating an echo profile signal of each echo signal, connected to said microphone; delay means for adding a variable delay to each echo profile signal, said variable delay increasing with the distance to said objects, connected to said echo profile detector; and a receive transducer connected to said delay means, acoustically coupled to an ear of said person, wherein said variable delay has a decreasing rate of increase.

2. Echo locating apparatus according to claim 1 including signal level control means coupled to said echo signal for increasing the level of said echo signal with increasing distance to the reflecting objects.

3. Echo locating apparatus according to claim 2 including a gain control transistor in said level control means, having a gain control input, coupled to said echo profile signal, and a ramp generator having a ramp output connected to said gain control input for controlling said gain with said ramp.

4. Echo locating apparatus according to claim 1 including means for generating an audible feedback pulse from said sound emitter for each sound burst, to said receive means.

5. Apparatus according to claim 1, wherein each of said sound bursts is a train of sound waves of supersonic frequency.

6. Apparatus according to claim 1, wherein said sound burst emitter includes means for emitting a beam of said sound bursts, and means for selectively varying the angle of said beam of sound bursts.

7. Apparatus according to claim 1, wherein said delay means include a plurality of parallel-connected shift registers having a shift clock input, a digital input and a digital output, an analog to digital converter for converting said echo profile signal to a digital signal, connected to said digital input; a digital to analog converter connected to said output; a voltage-controlled oscillator having a frequency control input for generating a variable shift frequency connected to said shift clock input; and a ramp generator having a ramp output connected to said frequency control input.

8. Apparatus according to claim 1, including an amplifier stage having a logarithmic gain function, for amplifying said echo signal.

9. Apparatus according to claim 1, including a bandpass filter for passing the frequency of said sound burst.

10. Apparatus according to claim 7, including a bandpass filter connected to the output of said digital to analog converter for generating a delayed echo profile signal.

11. Apparatus according to claim 1, wherein said sound burst emitter includes a first timer for generating a start pulse for said sound burst, a second timer being responsive to said first timer for timing the duration of said sound burst, a frequency generator for generating the frequency of said sound burst, being responsive to said second timer, and a transmit transducer connected to said frequency generator for generating sound waves for said sound burst.

12. Apparatus according to claim 11 wherein said sound burst emitter includes a horn for directing said sound bursts as a beam of directed sound bursts.

13. Apparatus according to claim 1 including a trigger connected to said sound burst emitter for manually controlling the emission of said sound bursts.

14. Apparatus according to claim 1, wherein said delay means include a clock-driven charge-coupled shift register having a shift clock input connected to said voltage-controlled oscillator.

15. Echo locating apparatus according to claim 1 including two of said receive channels, each channel coupled to a respective ear of said person for providing binaural reception of said echoes.

16. Apparatus according to claim 15, wherein said delay means include a plurality of parallel-connected shift registers having a shift clock input, a digital input and a digital output, an analog to digital converter for converting said echo profile signal to a digital signal, connected to said digital input; a digital to analog converter connected to said output; a voltage-controlled oscillator having a frequency control input for generating a variable shift frequency connected to said shift clock input; a ramp generator having a ramp output connected to said frequency control input; wherein said voltage-controlled oscillator, said ramp generator and said fixed delay circuit are common to said two receive channels.

17. Echo locating apparatus according to claim 1 including signal chopping means for chopping said echo profile signal at a chopping frequency varying with the distance to the reflecting objects, coupled to said delay means.

18. Echo locating apparatus according to claim 17, including a voltage controlled oscillator in said signal chopping means, coupled to said delay means for varying said chopping frequency as a function of said variable delay.

19. Echo locating apparatus according to claim 18 including a voltage controlled oscillator and a frequency divider connected to said voltage controlled oscillator for dividing said chopping frequency at a given division ratio.

* * * * *